US00PP11436P

United States Patent [19]

Funanaka

[11] Patent Number: Plant 11,436

[45] Date of Patent: Jul. 4, 2000

[54] APPLE TREE NAMED 'RYOKA'

[75] Inventor: Kazutaka Funanaka, Nanyo, Japan

[73] Assignee: Nakajima Tenkoen Co., Ltd., Higashine, Japan

[21] Appl. No.: 08/730,731

[22] Filed: Oct. 11, 1996

[30] Foreign Application Priority Data

Oct. 11, 1995 [JP] Japan ..... 7-8207

[51] Int. Cl.[7] ..... A01H 5/00

[52] U.S. Cl. ..... Plt./161

[58] Field of Search ..... Plt./34.1, 161

*Primary Examiner*—Howard J. Locker
*Assistant Examiner*—Melissa L. Kimball
*Attorney, Agent, or Firm*—Armstrong, Westerman, Hattori, McLeland & Naughton

[57] ABSTRACT

An early to mid-season apple tree variety, *Malus Pumila Mill. var., domestica*, bearing medium to large fruit which is red overall, easily coloring to the calyx end, and having slightly coarse flesh which is sweet and juicy with many water cores at maturity.

8 Drawing Sheets

The present invention relates to a new and distinct variety of apple tree, *Malus Pumila Mill. var., domestica*, which is an early to mid-season apple cultivar, with easy coloring and good taste. This new and distinct cultivar is derived from a seedling discovered by K. Funanaka on his orchard. In 1981 he discovered a two-year old apple seedling on his orchard which is cultivated with 'Fuji' and 'Starking Delicious', and grew the seedling on his orchard. In 1988, the tree first produced 2–3 fruits. The inventor noticed that the fruit was very sweet with a water core in the flesh, and he then propagated and produced some trees of the seedling on 'Maruba' rootstocks for confirmation of stability of its characteristics. He observed the characteristics of the seedling and confirmed the stability and uniformity of the fine fruit characteristics. The fruit is of medium to large size (350–400 g), uniformly oblong, covered with red overall and easily coloring to the calyx end. The flesh is slightly coarse, sweet and juicy. Upon ripening, many water cores are produced in the flesh. 'Ryoka' matures mid- to late September, 15–20 days earlier than 'Beni Shogun' ('Heisei Fuji') (U.S. Plant Pat. No. 7997).

DETAILED DESCRIPTION OF VARIETY

Figure 1:
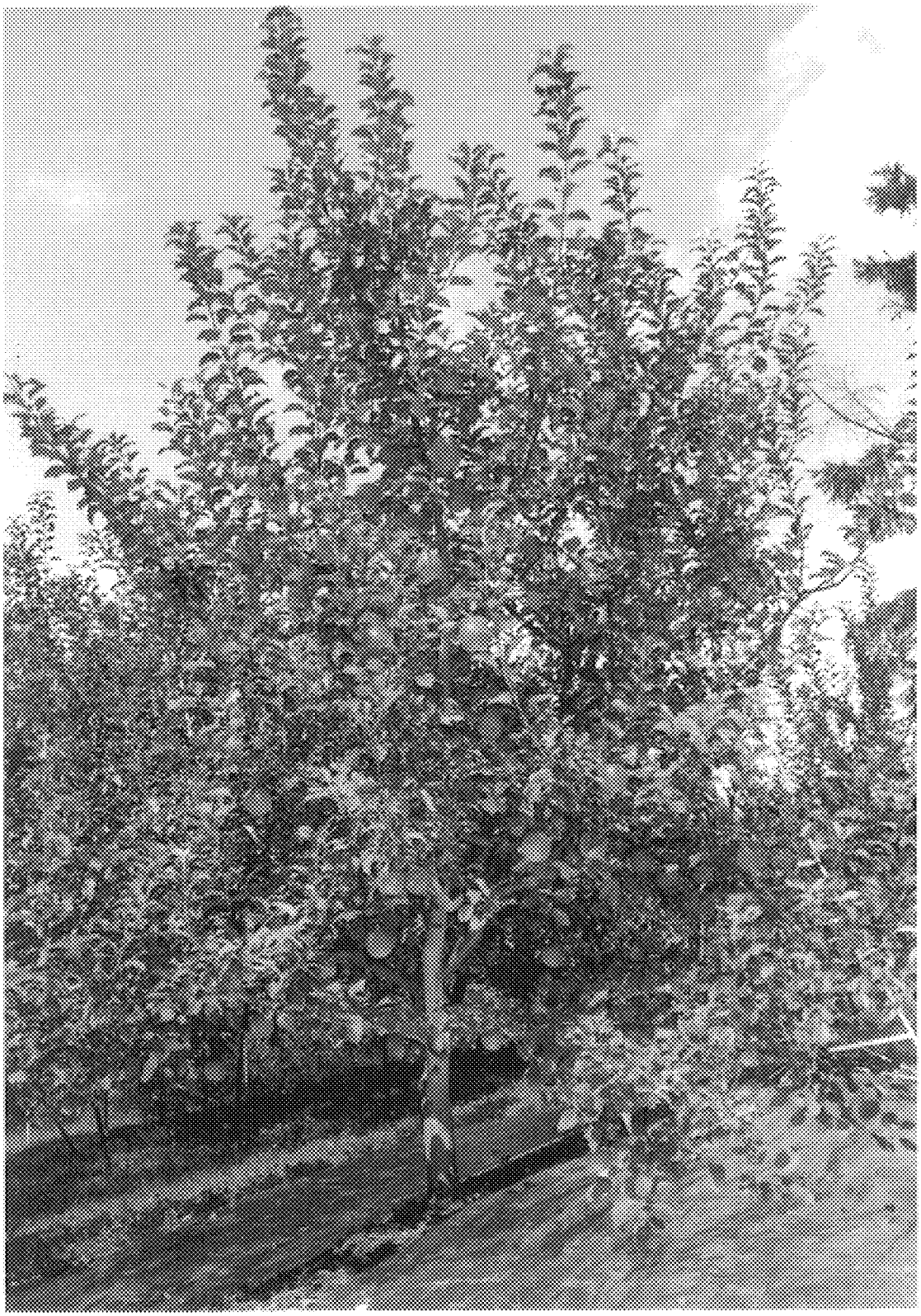
FIG. 1 shows a tree of 'Ryoka'.
Figure 2:
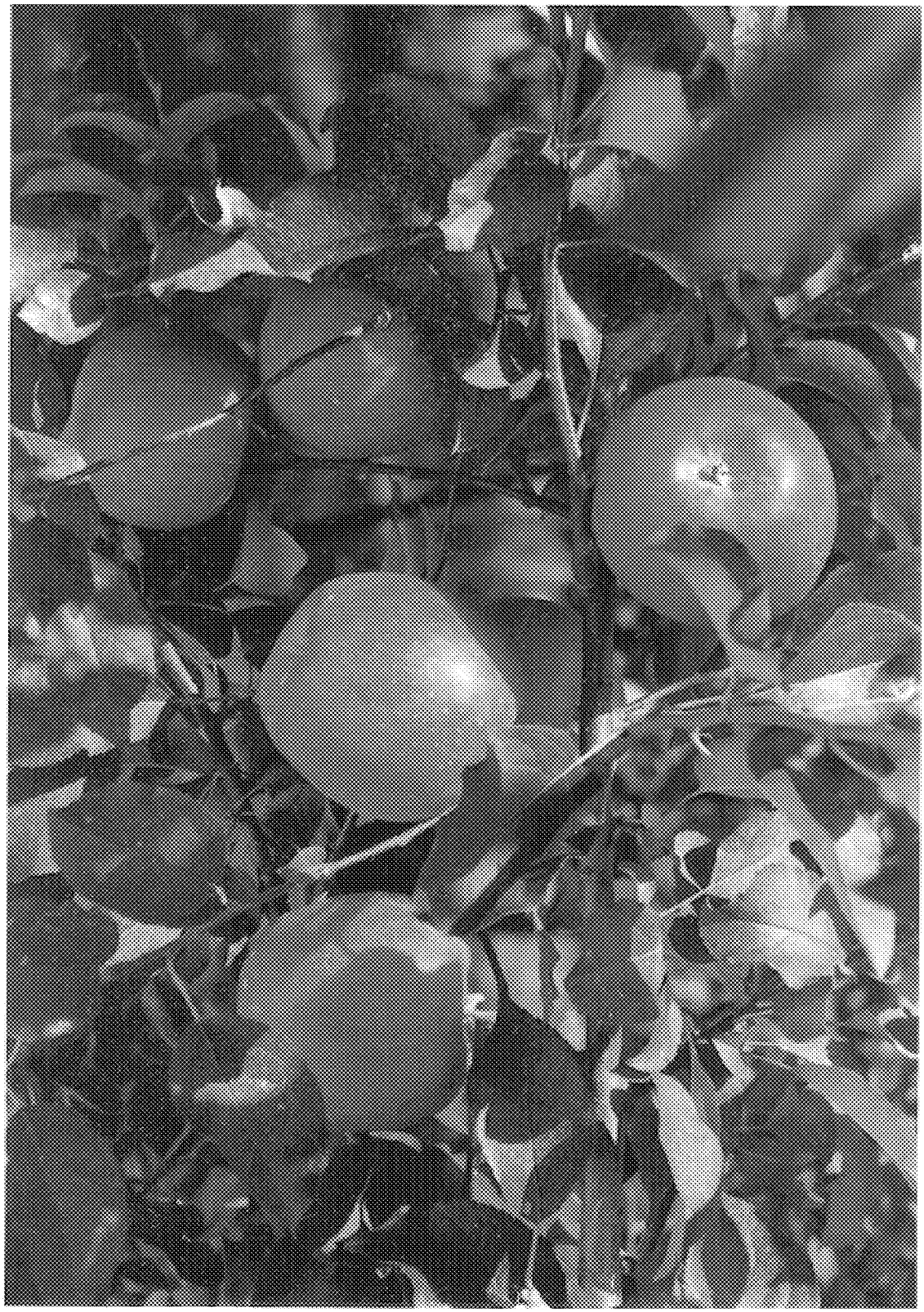
FIG. 2 shows a branch of 'Ryoka'.
Figure 3:
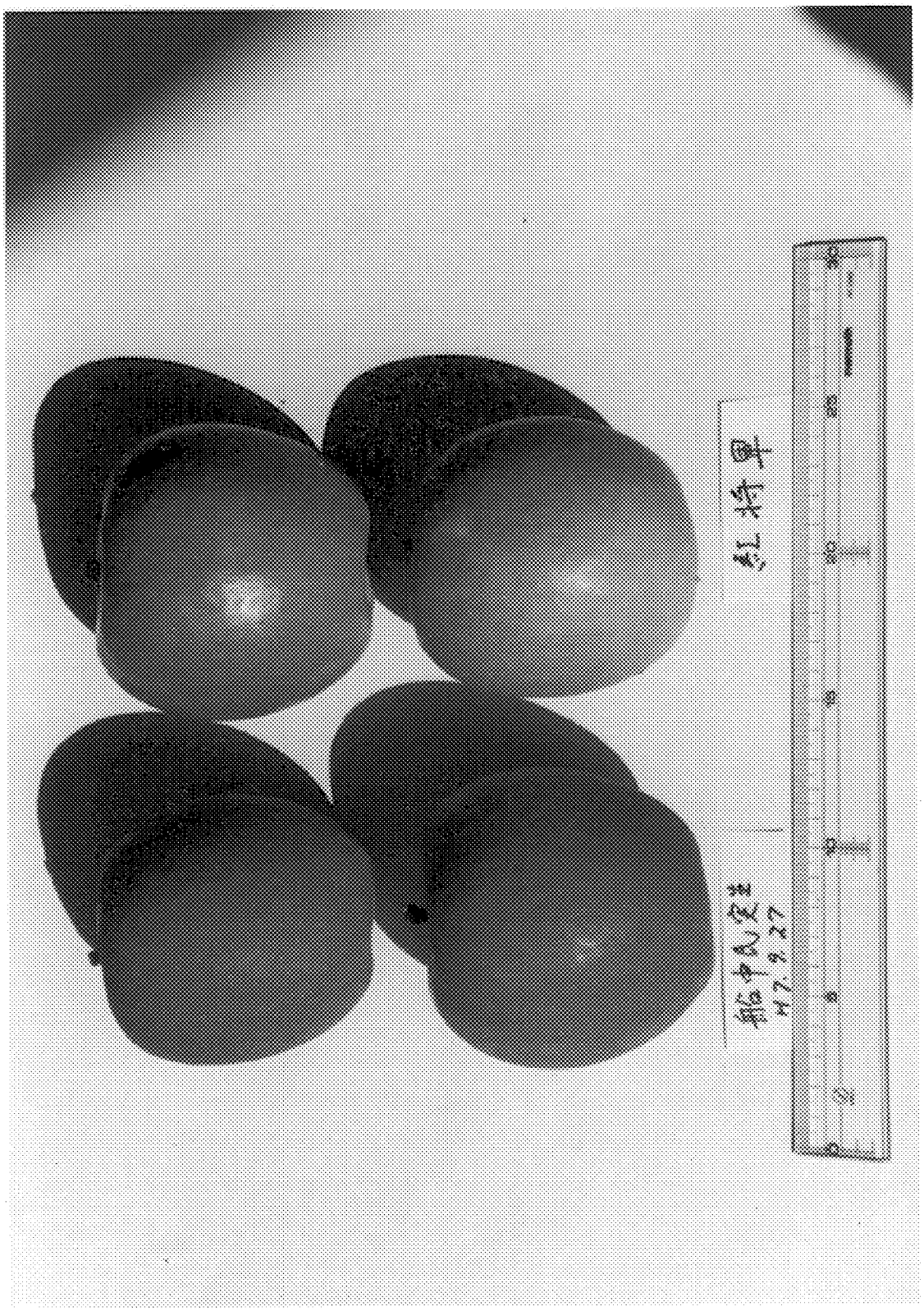
FIGS. 3, 4 and 5 show 'Ryoka' apples (left) compared with 'Beni Shogun' apples (right) from the side, upper and under views, respectively.
Figure 4:
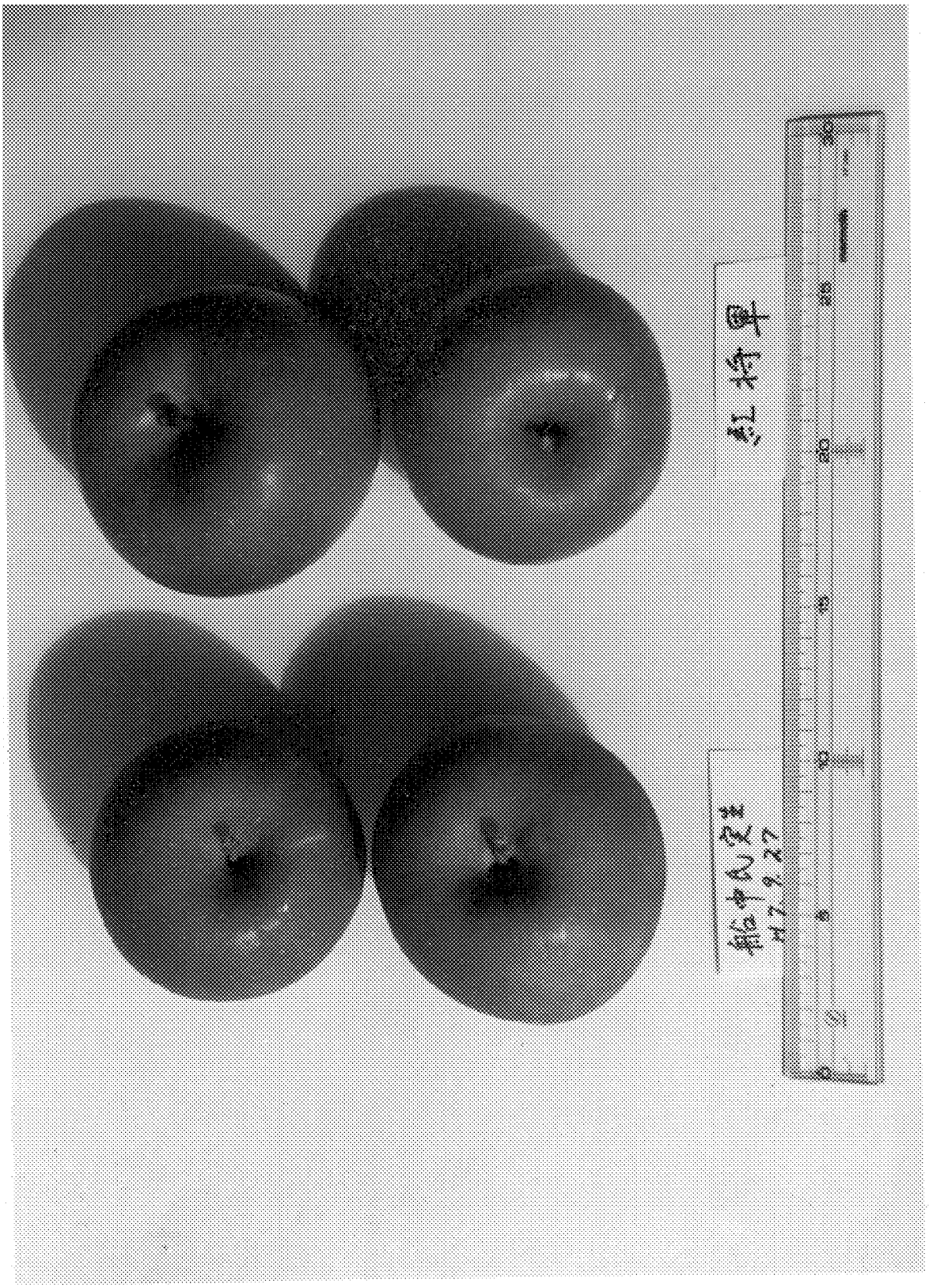
Figure 5:
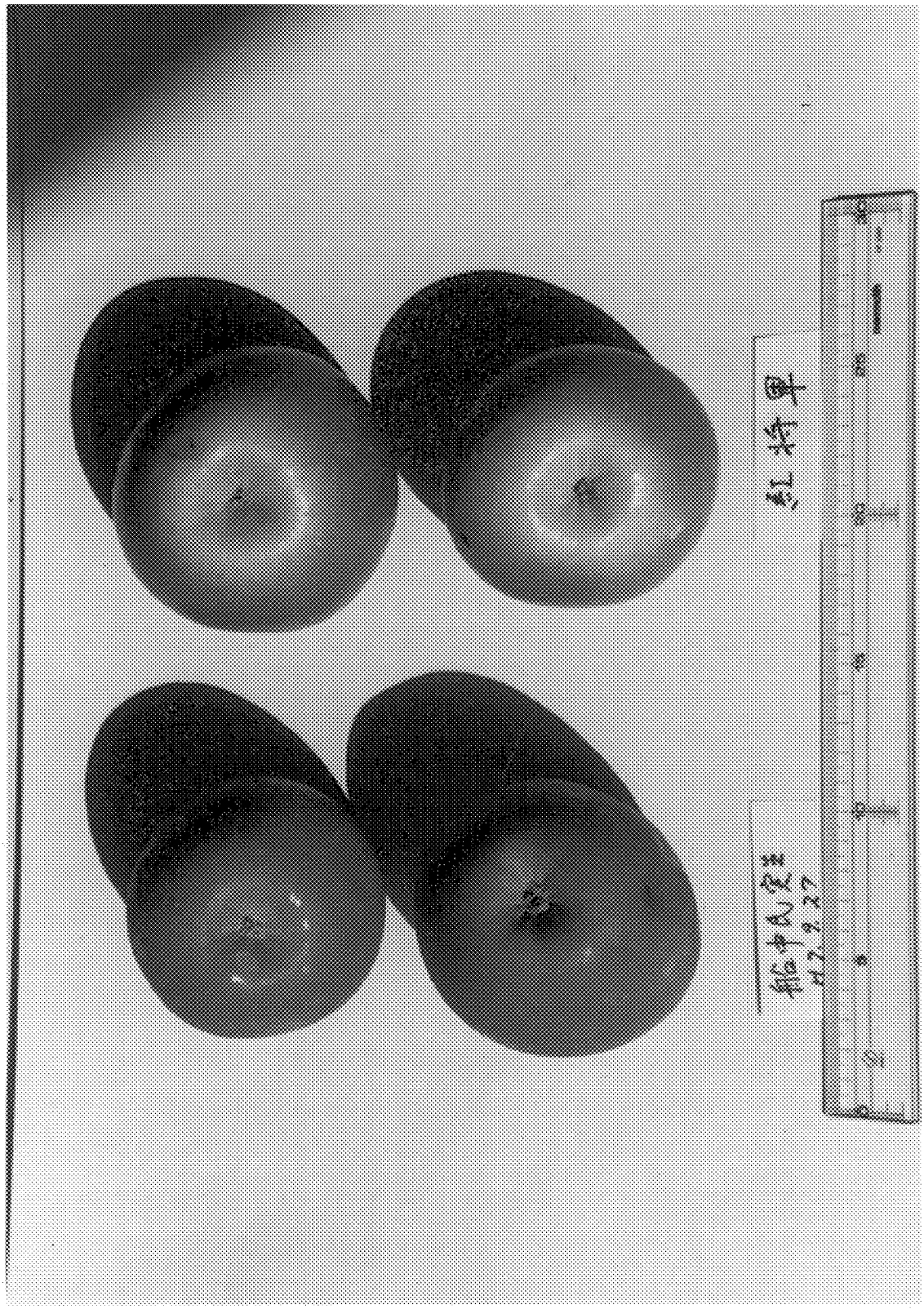
Figure 6:
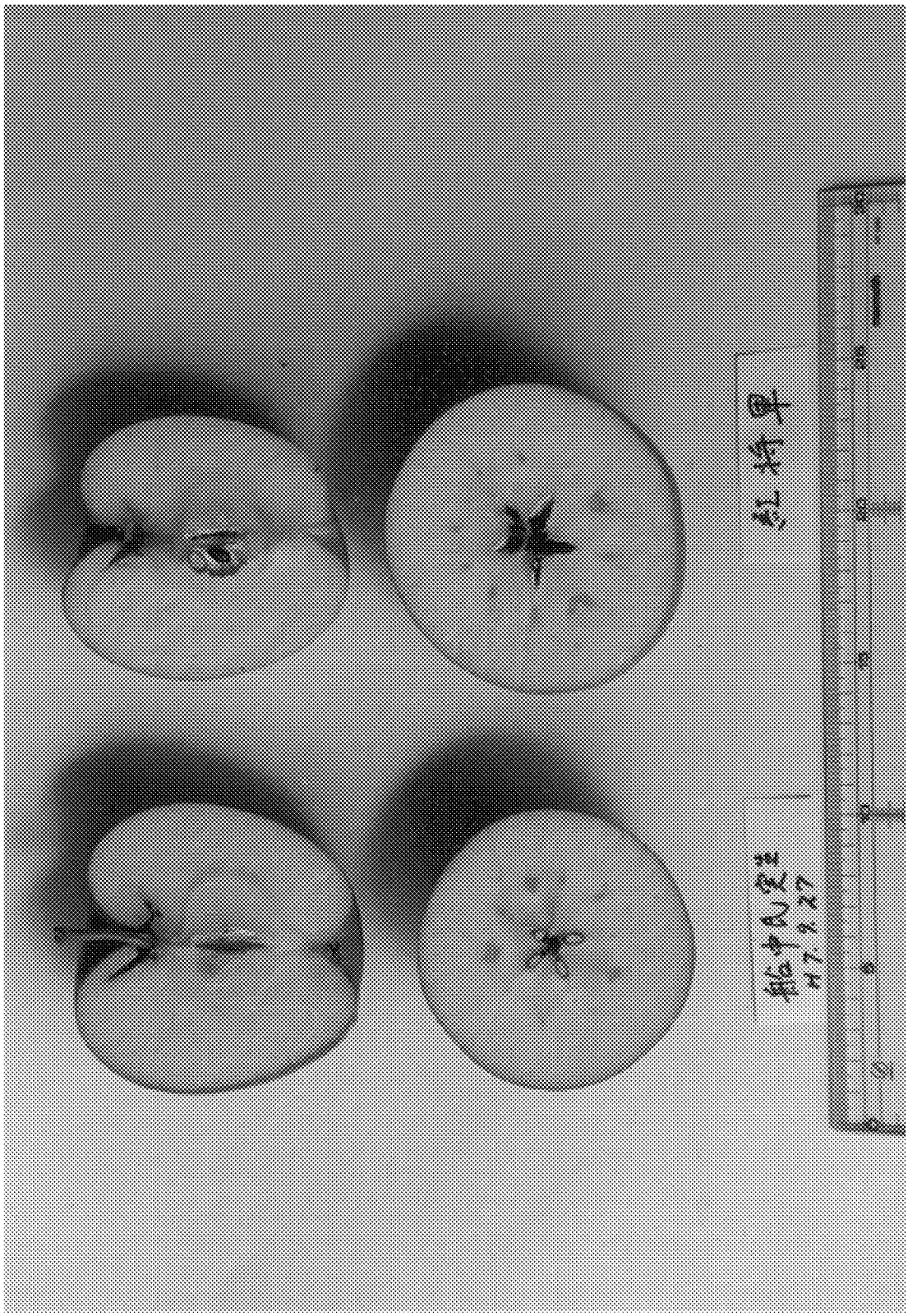
FIG. 6 shows the longitudinal and cross section of 'Ryoka' apples (left) compared with 'Beni Shogun' apples (right)
Figure 7:
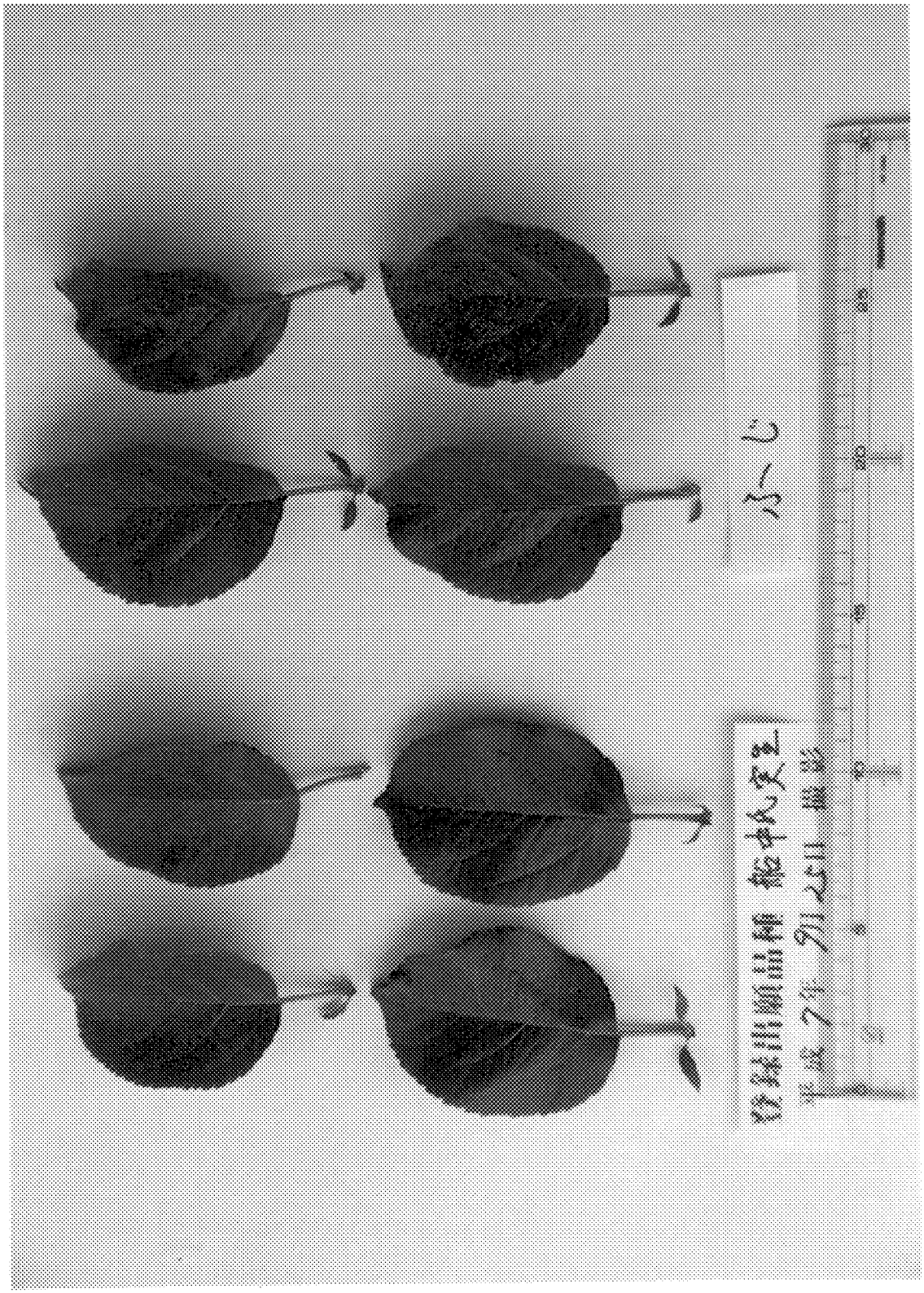
FIGS. 7 and 8 show the upper and lower leaf surfaces of 'Ryoka' (left) and 'Fuji' (right).
Figure 8:
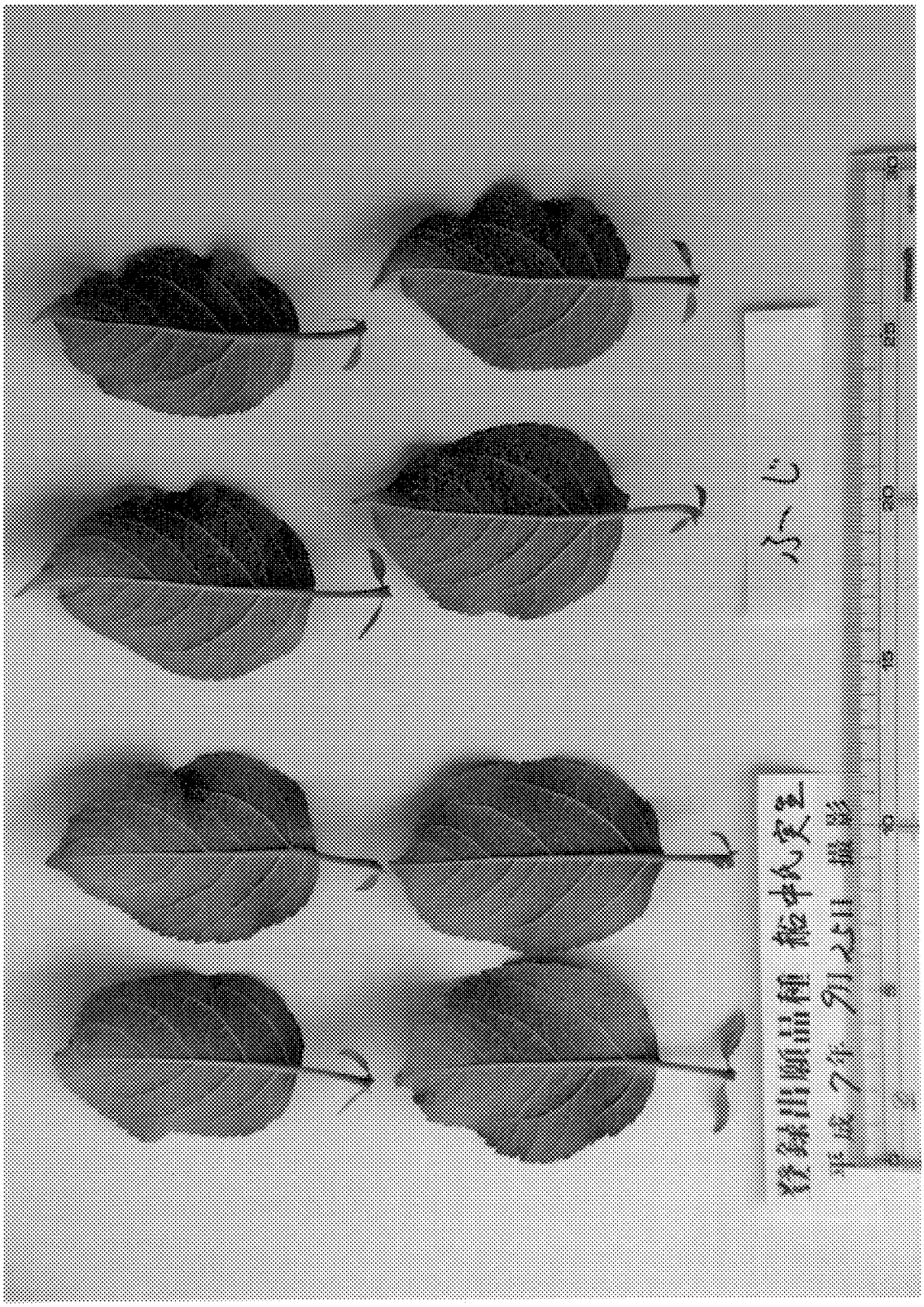

The characteristics of the new variety Ryoka are as follows, with color code numbers presented according to The Japanese Horticultural Society (JHS) color chart and the ISCC-NBS color chart.

Tree

Tree height: Medium.
Tree spread: Medium.
Branching density: Medium.
Tree habit: Slightly spreading, with fruit on spurs.
Habit of branches: Spreading tendency, with medium vigor. Supplemental support of branches is not necessary.

Although fairly large fruit (400–500 g) are obtained by appropriate thinning, the branches are strong enough to support the fruit.

Dormant shoot: Shoot is dark reddish brown (JHS No. 1009; ISCC-NBS dark reddish brown) on sunny side, and grayish brown (JHS No. 1919; ISCC-NBS grayish yellow brown) on under side. Surface of shoot is covered with round to oval medium size lenticels (diameter about 1 mm) and wax.

Current season shoot: Shoots are slightly wavy, internode is of medium length (2.9 cm) with pubescence. Leaves attach to shoot upward.

Leaf: Leaf is of medium size (length 9.0 cm, width 6.1 cm), dark yellow green (JHS No. 3509; ISCC-NBS moderate olive green), with crenate leaf margin. Petiole is of medium length (2.5 cm) with pubescence.

Flowering

Date of bloom: In Nan-yo City, Yamagata Prefecture, Japan:
*Start of bloom.*—May 13, 1996,
*Full bloom.*—May 18, 1996. Bloom time is almost the same as for Fuji variety. Pollination can be by 'Fuji' trees.

Days from bloom to fruiting: Around 125–135 days.

Fruit

Shape: Fruit is of medium to large size (350–400 g in weight), of uniformly oblong shape (length 89.6 mm, diameter 93.9 mm) with a slightly narrow and shallow cavity end. Ribbing on fruit is absent. Aperture of calyx end is closed.

Color: Fruit is covered with strong red color (JHS No. 0414; ISCC-NBS strong red) over color and bloom, easily coloring to the cavity end. The ground color of the fruit is yellowish green (ISCC-NBS). The fruit skin colors to strong red in gradation without stripes. The calyx end of the fruit colors to red at harvest time, a tendency more pronounced than in 'Fuji'. There is a little rust on the fruit surface. Fruit skin is smooth, medium glossy. Lenticels on skin are round to irregular in shape and of medium size (diameter about 1 mm). Fruit stalk is long (2.6 cm) and of medium thickness (2.8 mm). Strength of fruit flavor is medium and less than for 'Starking Delicious'.

Flesh: Flesh is pale yellow (JHS No. 2503), sweet (sugar content 12.6%, pH 3.78) with excellent taste. It produces many water cores in flesh at maturity. Firmness of flesh is medium (11–13 lb, average 12.06 lb). Texture is coarse and very juicy. Taste is intermediate between 'Fuji' and 'Starking Delicious'.

Seeds: length 8.14 mm, width 4.53 mm, side 3.01 mm. Seed number per fruit is on the average 11 seeds (8–17 seeds).

Maturity season: 'Ryoka' matures mid-September in Nan-yo City, Yamagata Prefecture, Japan, 3 days after 'Tsugaru' and 15–20 days earlier than 'Beni Shogun'. The fruit can be stored for almost half a month on the tree, and does not undergo mealy breakdown but develops a water core increase. The keeping quality of the fruit under ordinary storage conditions is long, a little longer than for 'Starking Delicious'. In refrigerated storage the fruit keeps longer than 'Starking Delicious' but not as long as 'Fuji'. The fruit taste does not decline for 1–2 months in refrigerated storage.

I claim:

1. A new and distinct variety of apple tree, substantially as illustrated and described herein, bearing medium to large fruit which is red overall, easily coloring to the calyx end, and having slightly coarse flesh which is sweet and juicy with many water cores at maturity.

* * * * *